United States Patent [19]

Goldberg et al.

[11] Patent Number: 6,090,997
[45] Date of Patent: Jul. 18, 2000

[54] METHOD AND COMPOSITION FOR PREVENTING SURGICAL ADHESIONS AND TISSUE DAMAGE EMPLOYING FLUORINATED POLYMERS

[75] Inventors: Eugene P. Goldberg, Mount Dora; James F. Kirk, Jacksonville; Lynn S. Peck, Gainesville, all of Fla.

[73] Assignee: University of Florida, Gainesville, Fla.

[21] Appl. No.: 09/247,559

[22] Filed: Feb. 10, 1999

[51] Int. Cl.⁷ .................. A61F 2/02; C08J 2/16; A61K 31/785
[52] U.S. Cl. .................. 623/11; 524/805; 424/78.06
[58] Field of Search .................. 514/57; 524/805; 424/78.06; 623/78.06

[56] References Cited

U.S. PATENT DOCUMENTS

| | | | |
|---|---|---|---|
| 5,256,731 | 10/1993 | Huth et al. | 524/805 |
| 5,350,573 | 9/1994 | Goldberg et al. | 424/78.06 |
| 5,941,909 | 8/1999 | Purkait | 623/11 |
| 5,980,625 | 11/1999 | Sawamura et al. | 106/35 |

*Primary Examiner*—Michael J. Milano
*Assistant Examiner*—Hieu Phan
*Attorney, Agent, or Firm*—Miles & Stockbridge; Dennis P. Clarke

[57] ABSTRACT

An improved method for preventing adhesions during surgery. Tissue surfaces and surgical articles involved in the surgery are coated with a solution of a hydrophilic, polymeric material prior to manipulation of the tissue during surgery. The polymeric material is (1) a substantially water-soluble polymer having at least one $C_nF_{2n+1}$ substituent wherein $n \geq 4$, having a molecular weight of less than about 60,000; (2) a pharmaceutically acceptable salt or complex thereof; or (3) mixtures thereof. The concentration of the aqueous solution of the polymeric material is in the range of from about 0.1% to about 5.0% by weight, the molecular weight and concentration having values such that the aqueous solution is capable of providing wet coatings on the tissue.

22 Claims, No Drawings

METHOD AND COMPOSITION FOR PREVENTING SURGICAL ADHESIONS AND TISSUE DAMAGE EMPLOYING FLUORINATED POLYMERS

RELATED APPLICATIONS

This application contains subject matter related to application Ser. No. 08/141,016 filed Oct. 26, 1993, which is a continuation-in-part of application Ser. No. 08/026,125 filed Mar. 3, 1993 (now U.S. Pat. No. 5,350,573 issued Sep. 27, 1994), which is a continuation of application Ser. No. 07/218,125 filed Jan. 8, 1992 (now abandoned), which is a division of application Ser. No. 07/696,960 filed May 8, 1991 (now U.S. Pat. No. 5,140,016 issued Aug. 18, 1992), which is a continuation of application Ser. No. 07/555,377 filed Jul. 19, 1990 (now U.S. Pat. No. 5,080,893 issued Jan. 14, 1992), which is a continuation of application Ser. No. 07/199,687 filed May 31, 1988 (now abandoned). Related subject matter is also contained in application Ser. No. 07/750,840 filed Aug. 29, 1991, application Ser. No. 03/141,017 filed Oct. 26, 1993, application Ser. No. 08/210,454 filed Mar. 21, 1994, and application Ser. No. 08/485,332 filed Jun. 7, 1995. The entire contents and disclosures of each of the above-identified applications and patents are incorporated herein by reference.

BACKGROUND OF THE INVENTION

1. Field of the Invention

The present invention relates to the improvement of surgical techniques and tissue-protective surgical solutions.

2. Discussion of the Prior Art

Adhesions of the tissues involved in surgery occasioned by manipulative trauma of the tissue surfaces during the surgery and other causes such as drying and ischemic trauma constitute one of the most serious post-operative complications of surgical procedures.

Although a variety of techniques have been proposed to reduce adhesions, the problem continues to plague the art and seriously compromise even the finest and most scrupulously performed surgeries. Prior attempts to alleviate the problem and the disappointing results attendant are described by Davis et al in Surgery, Vol. 2, p. 877 (1937); Gozalez, Surgery, Vol. 26, p. 181 (1949); Hunter et al, J. Bone Joint Surg., Vol. 53A, p. 829 (1971); Ellis, Surg. Gynecol. Obst., Vol. 133, pp. 497–511 (1971); Lindsay et al, In Verdan, C. (ed.); Tendon Surgery of the Hand, London, Churchill Livingstone, pp. 35–39 (1979); Potenza, J. Bone Joint Surg., Vol. 45A, p. 1217 (1963); Verdan, J. Bone Joint Surg., Vol. 54A, p. 472 (1972); St. Onge et al, Clin. Orthop., Vol. 148, pp. 259–275 (1980); Thomas et al, Clin. Orthop., Vol. 206, pp. 281–289 (1986); Weiss et al, Bull. Hosp. Jt. Dis. Orthop. Inst., Vol. 46(1), pp. 9–15 (1986).

Goldberg et al [Arch. Surg., Vol. 115, pp. 776–780 (1980)] describe the use of certain hydrophilic, polymeric solutions (Povidone polyvinylpyrrolidone K-30 PVP, and dextran) to coat tissue exposed to drying and/or manipulative peritoneal trauma, as well as the surgical articles and the like, which contact the tissue before and during surgery to prevent adhesions. Although the materials and methods of Goldberg et al showed some improvement over other research studies in which hydrophilic, polymeric solutions were used to attempt to reduce the incidence of surgical adhesions, there still exists significant need for improvement.

A distinct disadvantage associated with the materials and methods of Goldberg et al and other prior art which has shown some benefit is the required use of highly concentrated solutions of the polymeric materials which makes practical use in surgery very difficult. Concentrated polymeric solutions (greater than about 10–15%), for example, the 25% PVP and dextran solutions used by Goldberg et al, become sticky due to drying during surgery on the surfaces of tissue, surgeons' gloves, instruments, and the like. This can seriously interfere with normal surgical procedures. High concentrations of PVP (K-30 molecular weight about 40,000) and dextran (molecular weight about 300,000) were required to achieve even some degree of tissue protection. Many studies prior to the report of Goldberg et al used lower concentrations of PVP, dextran or other water-soluble polymers which were even more ineffective. For example, Ellis [supra] has stated that "use of PVP was accompanied by a slightly greater incidence of adhesions" in a rat peritoneal adhesions study. He also states that because "such macromolecular solutions as plasma or dextran are known to be absorbed rapidly through functional lacunas on the under surface of the diaphragm" and "[i]t is therefore probable that any effect of PVP or any other macromolecular solution introduced into the peritoneal cavity could only be transitory." In the study by Berquist [Eur. Surg. Res., Vol. 9, p. 321 (1977)] using 10% dextran-70 (molecular weight 70,000) and 1% hyaluronic acid (molecular weight unknown), it was reported that there was "no difference between control and treated groups" for adhesions in rat and rabbit studies. Even attempts to use the relatively low molecular weight dextran-70 at very high concentrations (32%) based on suggestions of some beneficial effect in reducing genital tract adhesions in female rabbits [Neuwirth et al, Am. J. Obst. Gynecol., Vol. 121, p. 420 (1974)] have not proven very successful. A commercial 32% (w/v) solution of dextran-70 was introduced as a hysteroscopy fluid around 1984, but recent studies have shown "no effect in reducing adhesions" using 32% dextran [Hadick et al, Military Medicine, Vol. 152, p. 144 (1987)].

Moreover, the use of such high concentrations may increase the expense of the surgical solutions and poses problems in preparing, purifying, stabilizing and storing solutions of such highly concentrated and often viscous solutions. For example, 32% dextran tends to crystallize "when subjected to temperature variations or when stored for long periods" [data sheet for commercial 32% dextran-70 solution].

Although the studies reported by Goldberg et al indicated some modest improvement in preventing adhesions using 25% PVP (molecular weight 40,000) and a slight improvement with 25% dextran (molecular weight 300,000) even using a surgical method involving coating of tissues and surgical implements before surgical manipulation, the materials and surgical solutions used were clearly impractical for clinical use in surgery.

In patent application Ser. No. 07/555,377 filed Jul. 19, 1990, now U.S. Pat. No. 5,080,893, there are described improved methods for preventing surgical adhesions in tissue by manipulation thereof during surgery comprising coating tissue surfaces involved in the surgery and/or the surfaces of surgical articles which contact the tissue surfaces during the surgery with an aqueous solution of a hydrophilic, polymeric material selected from the group consisting of water-soluble, biocompatible, pharmaceutically acceptable polypeptides, polysaccharides, synthetic polymers, salts and complexes thereof and mixtures thereof prior to manipulation of the tissue during the surgery, the improvement wherein the hydrophilic, polymeric material is of high molecular weight (greater than 500,000) and the solution contains from about 0.01% to about 15% by weight of the polymeric material.

The application further describes certain compositions, specifically adapted for coating the surfaces of tissues involved in surgery and preferably also the surfaces of articles which contact the tissue surfaces during the surgery to prevent surgical adhesions in the tissue by manipulation or drying thereof during surgery, consisting essentially of a pharmaceutically acceptable aqueous solution of a hydrophilic, polymeric material of high molecular weight (greater than 500,000) selected from the group consisting of pharmaceutically acceptable polypeptides, polysaccharides, synthetic polymers and salts and complexes thereof and mixtures thereof. Where the polymeric material is a polysaccharide, solutions according to the invention containing from about 0.01 to less than about 1% by weight of the polysaccharide have been found to be highly advantageous. Where the polymeric material is a polypeptide or synthetic polymer, solutions according to the invention containing from about 0.01 to less than about 15% by weight thereof may be employed.

An additional embodiment of the invention described therein comprised surgical articles, surfaces of which are adapted for contacting tissue surfaces during surgery having a coating thereon formed from a composition described above.

Surgical adhesions, however, are only one of the several types of complications which arise from the damage inflicted to tissue during surgical procedures. In addition to the formation of post-operative adhesions, tissue trauma during surgery can lead to a host of other potentially serious complications during and following surgical procedures, including:

(1) excessive blood vessel damage with increased bleeding during surgery and with greater risk of postoperative hemorrhage;

(2) enhancement of (acute) post-operative inflammation with prolongation of healing and damage to adjacent healthy tissues, as well as increased potential for chronic prolonged inflammation with associated secondary complications, pain, and the like;

(3) compromised wound healing with excessive scar tissue, of particular importance in orthopedic and plastic surgery;

(4) damage to organs and tissues which can result in impaired organ function, i.e., kidneys, liver, heart, lungs, and the like;

(5) blood vessel damage which can reduce blood supply with partial ischemia of muscle tissues and organs, leading to compromised function of muscle and vital organs, which is a life-threatening situation for heart muscle damage; and (6) increased susceptibility to acute and chronic infections due to preferential adherence and growth of pathogens on damaged tissue sites (post-operative staph and pseudomonas infections) with increased difficulty in treatment, slower recovery and greater chance of life-threatening systemic sepsis.

All of the above tissue damage related complications can result in longer hospitalization, patient discomfort, greater risk of morbidity and mortality, greater incidence of re-hospitalization and corrective surgery with associated patient risks, and higher health care costs.

Desiccation and abrasion tissue damage during surgery can lead to a variety of pathological surgical and postoperative complications. Damage due to desiccation and abrasion of the ovaries often results in formation of a thin fibrous membrane over the surface of the organ. Often this membrane is difficult to see with the unaided eye, yet it can act as a physical barrier to prevent transport of an egg to the Fallopian tube, thus preventing fertilization.

Prosthetic devices and implants such as heart valves, ventricular assists, vascular grafts, ligaments, tendons, corneas, skin grafts, muscle grafts and the like which are derived entirely or in part from animal or human tissue or organs are subjected to handling and manipulation in the normal course of harvesting, processing, manufacturing, shipping and storage of prostheses. Some specific examples of such bioprostheses include, but are not limited to, porcine heart valves, fetal tissue derived vascular grafts (e.g., from umbilical tissue), fetal neurological tissue, electrically activated muscle blood pumps (e.g., ventricular assist devices), and the like. The manipulation of these tissue derived bioprostheses and organ transplants can damage tissues, e.g., by desiccation or abrasive trauma, and thereby adversely affect in vivo biophysical or biochemical properties and reduce the safety and efficacy of the bioprosthesis or organ transplant. Organ and tissue transplants such as hearts, lungs, kidneys, livers, corneas, tendons and the like can be similarly damaged by the normal manipulation that occurs with harvesting, storing, preparing, processing, shipping and implanting organs, tissues or composite bioprostheses into recipient patients.

It is an object of the present invention to provide an improved method of preventing surgical adhesions during surgery.

It is another object of the present invention to provide improved compositions and methods for protecting tissue and preventing tissue damage in surgery.

It is an additional object of the present invention to provide improved methods and compositions for protecting human and animal derived tissues and organs during the manipulations that occur during harvesting, processing, storing, shipping and implantation thereof from trauma and damage which can result in impaired organ or tissue function or induce undesirable biological behavior.

Finally, it is a further object of the present invention to provide improved compositions and methods for protecting those parts of bioprostheses derived from animal or human tissues or organs from trauma and damage during the harvesting thereof and the manufacture, processing, storing, manipulation, shipping and implantation of the bioprosthesis, which trauma or damage could result in impaired bioprosthesis function or induce undesirable biological behavior.

SUMMARY OF THE INVENTION

An embodiment of the present invention comprises a method of preventing post-operative surgical adhesions of tissue and protecting tissue and preventing tissue damage in surgery comprising providing the tissue surfaces involved in the surgery with a wet coating of a physiologically acceptable aqueous solution of a hydrophilic, polymeric material prior to manipulation of the tissue during the surgery, wherein:

(a) the polymeric material is (1) a substantially water-soluble polymer having at least one $C_nF_{2n+1}$ substituent wherein $n \geq 4$, having a molecular weight of less than about 60,000; (2) a pharmaceutically acceptable salt or complex thereof; or (3) mixtures thereof; and (b) the concentration of the aqueous solution of the polymeric material is in the range of from about 0.1% to about 5.0% by weight, the molecular weight and concentration having values such that the aqueous solution is capable of providing wet coatings on the tissue.

Another embodiment of the present invention is a method of protecting tissue and preventing tissue damage in surgery comprising providing surfaces involved in the surgery with a wet coating of a physiologically acceptable aqueous solution of a hydrophilic, polymeric material prior to manipulation of the tissue during surgery, wherein:

(a) the polymeric material is (1) a substantially water-soluble polymer having at least one $C_nF_{2n+1}$ substituent wherein $n \geq 4$, having a molecular weight of less than about 60,000; (2) a pharmaceutically acceptable salt or complex thereof; or (3) mixtures thereof; and (b) the concentration of the aqueous solution of the polymeric material is in the range of from about 0.1% to about 5.0% by weight, the molecular weight and concentration having values such that the aqueous solution is capable of providing wet coatings on the tissue.

Yet another embodiment of the present invention comprises a surgical article, surfaces of which are adapted for contacting tissue surfaces during surgery having a coating thereon formed from one of the compositions described above.

A further embodiment of the present invention relates to a method of protecting from damage tissues or organs during the harvesting thereof from animals or humans, the manufacture therefrom of bioprostheses and the subsequent manipulations and implantations of the bioprostheses in animals or humans, comprising providing the tissue or organ surfaces with a wet coating of a physiologically acceptable aqueous solution of a hydrophilic, polymeric material prior to and during the harvesting, manufacture of bioprostheses, manipulations and implantations thereof, wherein:

(a) the polymeric material is (1) a substantially water-soluble polymer having at least one $C_nF_{2n+1}$ substituent wherein $n \geq 4$, having a molecular weight of less than about 60,000; (2) a pharmaceutically acceptable salt or complex thereof; or (3) mixtures thereof; and (b) the concentration of the aqueous solution of the polymeric material is in the range of from about 0.1% to about 5.0% by weight, the molecular weight and concentration having values such that the aqueous solution is capable of providing wet coatings on the tissue.

DETAILED DESCRIPTION OF THE INVENTION

The present invention is predicated on the discovery that surgical adhesions and damage to tissue from surgical procedures may be prevented to a far greater extent than previously achieved by ensuring pre-coating of the involved tissues and surfaces of surgical articles prior to the surgical manipulation thereof with the above-described solutions.

The viscosity of polymeric solutions is normally determined by the molecular weight and concentration of the polymer in the solution. This relationship is empirically described by the equation $\eta$ MC [Ferry, "Viscoelastic Properties of Polymers," pages 541–542, J. Wiley & Sons, New York (1970)]. Accordingly, for most polymers, as either or both molecular weight and concentration of the polymeric material increase, the viscosity of the solution likewise increases. However, for ionic polyelectrolyte polymers such as hyaluronic acid or carboxymethyl cellulose, molecular associations in solution can increase viscosities at lower concentrations or at lower molecular weights. It has been discovered that the ability of the solutions of polymeric material to prevent tissue damage and thereby reduce adhesion formation is related to the viscosity of the solution, not just molecular weight or concentration. Thus, relatively low molecular weight polymeric materials, especially those which associate in solution to enhance viscosity, at the appropriate concentrations, can provide sufficient viscosity to protect tissue from surgical damage and, therefore, adhesion formation.

The novel lower molecular weight polymer compositions of this invention unobviously reduce the incidence of surgical adhesions and damage to tissue from surgical procedures to a far greater degree than would be expected from a reading of the extensive literature in this field.

It has been found, as demonstrated hereinbelow, that the use of the lower molecular weight hydrophilic, polymeric solutions of this invention, used in the relatively low concentration range described herein, results in unexpected high viscosities and a significant decrease in the risk of surgical adhesions and tissue damage. It is believed that this unexpected enhancement of solution viscosity at low molecular weights and low concentrations for hydrophilic polymer substituted with perfluorocarbon groups results from molecular associations in aqueous solutions.

The unexpected benefit of using the polymer compositions of this invention during surgery with pre-coating of the involved tissue has been clearly shown to give far better results than post-operative or post-tissue manipulative treatment or coating.

Furthermore, the surprisingly advantageous tissue-protective, adhesions preventive properties of the compositions of this invention have been demonstrated when used to coat tissue prior to surgical manipulation even when conventional irrigating solutions are subsequently used during surgery.

For purposes of the present invention, the following definitions are applicable herein.

"Surfaces" refers to the surfaces of all tissue involved in and subject to manipulation by a foreign object during surgery or exposed to traumatic drying in the surgical field, as well as the surfaces of all surgical articles used in surgery and which may contact the involved tissue.

"Involved tissue surfaces" refers to all tissue involved in and subject to manipulation by a foreign object during surgery, exposed to traumatic drying in the surgical field or exposed to gases such as $CO_2$ during endoscopic procedures.

"Surgical articles" refers to all instruments, devices, accessories, swabs, sponges, gauzes, gloves, sutures, and the like, used in surgery and which may contact the involved tissue.

"Surgery" refers to all invasive surgical techniques including endoscopic procedures which expose tissue subject to surgical adhesions.

"Manipulation" refers to all contact with involved tissue which causes surgical adhesions or tissue damage.

"Surgical adhesions" refers to the collagenous connective tissue which develops post-operatively after manipulative trauma to the involved tissue. Also defined by this term are adhesions produced from involved tissue due to drying and/or ischemic trauma during the surgical procedure.

The term "tissue damage" refers to an insult to the surface of hard and soft tissues and organs that results in a temporary or permanent effect on the physical, physiological or biochemical state of the tissue such as eliciting a wound healing or inflammatory response, discoloration due to desiccation or abrasive trauma, visual or microscopic damage to epithelial or endothelial surfaces, changes in tissue mechanical properties, i.e., embrittlement due to drying and changes in metabolic function of surface cell layers, e.g., enzyme function.

"Coating formed from the aqueous composition" refers to the "wet" coatings formed on the coated surfaces using the aqueous composition, as well as coatings formed from the aqueous composition which are dried and may be subsequently re-wetted to produce the wet coating.

The term "prosthesis" refers to a device for replacing a part of the body of a human or animal.

The term "bioprosthesis" refers to a prosthesis composed at least in part from human or animal derived tissues or organs.

In general, there is extensive literature on attempts to use various hydrophilic, polymeric solutions to prevent surgical adhesions by applying such solutions to the tissue surfaces in the surgical field following manipulative procedures and tissue trauma and just prior to wound closure. The concept guiding such studies has been that the viscous polymeric solutions might afford a protective barrier to bridging of the traumatized tissues by collagenous connective tissue (adhesions). Polyvinylpyrrolidone (PVP), carboxymethylcellulose (CMC), dextran (dex) and hyaluronic acid (HA) have all been investigated, but no clinically practical results have been achieved.

The present invention is predicated on the discovery that a major improvement in the prevention of adhesions and tissue damage is surprisingly achieved with certain aqueous hydrophilic, polymeric solutions of lower molecular weights and lower concentrations to provide sufficient viscosity using a method of tissue protection involving the application of the polymeric solution to the tissue before surgical manipulative procedures are initiated. This combination of materials and method of use results in uniquely successful tissue protection and prevention of surgical adhesions and overcomes the drawbacks of the prior art where either (1) the polymers used (i.e., PVP or dextran) have been of molecular weights less than 500,000 necessitating high concentrations (greater than 20%) to have sufficient viscosity to provide any beneficial effect and, therefore, exhibiting difficult physical handling properties during surgery and/or (2) the solutions have been used by a method involving coating of tissues at the conclusion of surgery, thus not affording the tissue protection during surgery which is provided by the method of this invention. Thus, by the combined use of (a) more dilute aqueous hydrophilic, polymeric solutions made possible with polymers having molecular weights less than 100,000 Daltons and concentrations less than 10% to provide sufficient viscosity to protect tissue surfaces from damage during surgery and (b) a method of use wherein the solution is used as a tissue protective coating at the beginning of and during surgery, it has been discovered that a major improvement in preventing surgical adhesions, which is clinically practical, is achieved.

This invention is predicated on the use of the novel viscous polymeric solutions described herein.

Unexpectedly, we have discovered that dilute solutions of the above-described fluoroalkyl substituted polymers with molecular weights of less than about 60,000 are effective at concentrations of up to about 5.0% by weight when used for surgical adhesions prevention and tissue protection by the method of the present application. Such solutions, therefore, represent efficient materials for the method of this invention because of the excellent biocompatibility, favorable non-Newtonian rheology and tissue coating by dilute solutions, practical cost for general surgical applications which may require 1–2 liters of the dilute solutions, and adhesion prevention qualities when combined with the method of use according to the present invention.

Virtually all types of surgery in which post-operative adhesions represent a significant complication (e.g., peritoneal, pericardial, obstetric, laparoscopic, endoscopic, gynecological, neurological, ENT, dental, arthroscopic, orthopedic, plastic, reconstructive, prosthetic, muscle or tendon) are susceptible to modification and improvement according to the present invention. Important examples include abdominal, thoracic, cardiovascular, ob/gyn and neurosurgical procedures, all of which are fraught with potentially severe post-operative complications which may be attributed to surgical trauma. In the case of cardiac surgery involving transplants, vascular repair and by-passes, valve replacements and the like, reoperations continue to increase every year with repeat coronary artery surgery comprising the majority of such reoperations. Post-operative pericardial adhesions from initial surgery are common and subject patients undergoing repeat cardiac surgery to substantial risks. Potential injury to the heart, great vessels and extracardiac grafts during resternotomy, as well as prolonged operative time, increase morbidity and mortality. Resternotomy is associated with as much as a 6% incidence of major vascular injury and a more than 35% mortality has been reported for patients experiencing major hemorrhage during resternotomy. A 50% mortality rate has been reported for associated injuries to aortocoronary grafts. Pediatric cardiac surgery is also associated with a very high incidence of reoperations. In view of the marked increase in cardiac surgery and reoperations and the potentially serious complications related to pericardial adhesions, prevention of such adhesions represents a major health care need. The significant reduction in pericardial adhesions as well as tissue damage made possible by the materials and method of this invention is illustrated in the following examples.

Peritoneal adhesions represent another major health care problem with potentially serious post-operative complications associated with all types of abdominal surgery, with a reported incidence of 50–90% for laparotomies. As indicated in the following examples, a dramatic reduction in abdominal adhesions is made possible and clinically practical by the use of the materials and method of this invention.

The hydrophilic, polymeric material may be dissolved in any suitable aqueous solution conventionally employed in surgery, e.g., Ringer's lactate, normal saline or any other iso-osmolar physiological medium.

EXAMPLES

It has been previously disclosed that sodium hyaluronate (HA) solutions showed significant reduction of post-operative adhesions formation when the HA solutions were used to pre-coat tissues and thereby reduce surgical trauma [Goldberg et al, Transactions of the 17th Annual Meeting of the Society for Biomaterials, p. 252 (1991)].

Animal Model

A rat cecal abrasion model, employing a constant force auto-abrader, was used to evaluate the solutions described herein over a range of viscosities and molecular weights. The auto-abrasion method was developed to cause reproducible and controlled tissue damage and for reproducibly inducing adhesion formation. The device utilizes a rotating spline shaft which is free to move vertically. The abrasion force is provided by the weight of the shaft and, since the shaft is free to move, slight hand movement will not change the abrading force. The shaft is connected to a battery-driven motor which turns the shaft at a constant rate. The abrading surface used in all experiments was Type VII surgical gauze (1.77 cm$^2$ surface area) secured to the end of the shaft. The cecum was secured during abrasion in a Teflon device containing a hole large enough to accommodate the abrading surface. The abrasion parameters were standardized to provide reproducible results. Abrasion force was 70 gm, the shaft was rotated for 60 revolutions at 140 rpm for each abrasion site, and the cecum of each animal was abraded proximally and distally on the anterior and posterior sides of the cecum for a total of four abrasion sites.

All experiments were performed using a random/blind protocol. Treatment solutions and animals were fully randomized so that animal groups were not done sequentially.

Experimental Protocol

Sprague Dawley female (200–250 gm) rats were anesthetized by an intramuscular injection of ketamine (100 mg/kg body weight) and xylazine (10 mg/kg body weight). The peritoneum of each animal was surgically exposed via a 4–5 cm mid-abdominal incision. Two ml of solution were used to coat the abdominal organs and the cecum was maneuvered out of the abdominal cavity with cotton swabs precoated with the test solution. The cecum was coated with an additional 2 ml of solution (1.0 ml on the anterior cecum and 1.0 ml on the posterior cecum) and abraded at four sites. The cecum was replaced in the abdominal cavity after abrasion, and the incision was closed. One week following surgery, the animals were sacrificed by $CO_2$ asphyxiation, the peritoneal cavity was accessed via a left paramedian incision and adhesions were graded according to the 0–4 scale.

All test solutions were formulated aseptically in phosphate buffered saline solution (PBS) adjusted to pH 7.0. PBS control groups were also included.

The percent of animals with significant adhesions were compared among the different treatment groups by Chi-square analysis. The data reported and analyzed refers to the number of animals with cecal adhesion scores of 2 or higher.

Hydrophilic, polymeric solutions have been extensively studied for reducing post-operative adhesion formation. These solutions generally were usually somewhat viscous, were applied in large volume to the surgical field at the end of surgery (therefore, after tissue damage had occurred) and were relatively ineffective. On the other hand, the solutions of this invention act to reduce adhesion formation by precoating surgical tissues during surgery, thus providing a viscoprotective barrier during surgery which reduces tissue trauma and adhesion formation.

Scale for Evaluation of Cecal Adhesions

0=No adhesions

1=Filmy adhesion

2=Mild adhesion with freely dissectable plane

3=Moderate adhesion with difficult dissection of plane

4=Dense adhesion with non-dissectable plane

Table 1 below summarizes data from tests employing a 1.1 wt. % solution of polyethylene glycol [PEG-F] terminated at both ends with $C_8F_{17}$:

$$[F_{17}C_8\!-\!(OCH_2CH_2)_{\overline{x}}OC_8F_{17}]$$

wherein x is such that the polymer has a molecular weight of about 35,000. Similar results are obtained for the analogous water-soluble $F_{13}C_6(OCH_2CH_2)_x OC_6F_{13}$ polymer, wherein the PEG segment has a molecular weight of about 35,000. Similar results are also obtained using other PEG-F polymers in which the F-substituents having C-chains in the range $C_6$ to $C_{20}$, the number of such perfluoro alkyl groups is one or more, and where the PEG segment has a molecular weight of 20,000 to 60,000.

Similar results are also obtained for other perfluoro alkyl-substituted water-soluble polymers of 20,000 to 60,000 molecular weights including: polyvinylpyrrolidone, polyacrylamide, polydimethylacrylamide, dextran, carboxymethylcellulose, hydroxypropylcellulose and poly (ethylene oxide/propylene oxide).

TABLE 1

| | | | | Cecal Adhesions | | | | | |
| | | | | ≧ Grade 2 | | 0 Incidence | | Meant Incidence++ | |
| Group | Treatment | Viscosity (cps)+ | # of Rats | % | # w/adhesions # animals/group | % | # w/adhesions # animals/group | (X ± SEM) | # adhesions # animals/group | % Diff. vs. PBS |
| --- | --- | --- | --- | --- | --- | --- | --- | --- | --- | --- |
| 1 | PBS | <1 | 10 | 80 | (8/10) | 10 | (1/10) | 2.1 ± 0.5 | (21/10) | — |
| 2 | 0.4% HA | 128 | 10 | 10 | (1/10) | 80 | (8/10) | 0.4 ± 0.3 | (4/10) | 88 |
| 3 | PEG $(C_8F_{17})_2$ | 414 | 10 | 10 | (1/10) | 70 | (7/10) | 0.4 ± 0.2 | (4/10) | 88 |

+Viscometer model -- RVTD-IICP; C/P 52: at 100 sec$^{-1}$, 25° C.
++Mean incidence = Total number of cecal adhesions (all grades)/number of animals in group.

This class of fluoro-substituted water-soluble polymers is unique in enabling the use of relatively low molecular weight polymers to obtain high solution viscosity because of the physical association in solutions of the fluorocarbon groups. A potentially important aspect of this class of polymers is that renal clearance (through the kidney glomeruli) is likely even for polymer chains which do not readily biodegrade since the renal clearance cut-off is usually at molecular weights of about 40,000–60,000.

Any suitable hyarophtilic, substantially water-soluble polymer having at least one attached substituent fluorocarbon group of the structure $C_nF_{2n+1}$, wherein n≧4, having a molecular weight below about 60,000 is suitable for the purposes of the present invention. Exemplary of such polymers are $[F_{17}C_8(OCH_2CH_2)_xOC_8F_{17}]$ wherein x is an integer such that the molecular weight of the molecule is about 35,000. Other examples include, but are not restricted to), fluorocarbon group modified polyacrylamides, polydimethylacrylamides, polyvinylpyrrolidones, neutral polysaccharides (i.e., dextran, hydroxyethylcellulose), ionic polysaccharides (i.e., chlondroitin sulfate, hyaluronic acid), and polypeptides, wherein the fluorocarbon group(s) are preferably, but not restricted to, perfluoro-$C_6$ to $C_{12}$ substituents. Furthermore, these substituent perfluorocarbon group(s) may be at the substrate water-soluble polymer chain terminus or at some appropriate graft site(s) along the chain.

What is claimed is:

1. A method of preventing post-operative surgical adhesions of tissue and protecting tissue and preventing tissue damage in surgery comprising providing said tissue surfaces involved in said surgery with a wet coating of a physiologically acceptable aqueous solution of a hydrophilic, polymeric material prior to manipulation of said tissue during said surgery, wherein:
   (a) the polymeric material is (1) a substantially water-soluble polymer having at least one $C_nF_{2n+1}$ substituent wherein $n \geq 4$, having a molecular weight of less than about 60,000; (2) a pharmaceutically acceptable salt or complex thereof; or (3) mixtures thereof; and
   (b) the concentration in said aqueous solution of said polymeric material is in the range of from about 0.1% to about 5.0% by weight; said molecular weight and concentration having values such that said aqueous solution is capable of providing wet coatings on said tissue.

2. The method of claim 1 wherein said polymeric material is polyethylene glycol terminated at both ends with $C_nF_{2n+1}$ groups wherein $n \geq 4$.

3. The method of claim 2 wherein said $C_nF_{2n+1}$ group is $C_8F_{17}$.

4. The method of claim 1 wherein said polymeric material is selected from the group consisting of polyacrylamides, polydimethylacrylanides, polyvinylpyrrolidones, neutral polysaccharides, ionic polysaccharides, polypeptides and mixtures thereof.

5. The method of claim 1 wherein said surgery is peritoneal, pericardial, abdominal, obstetric, laparoscopic, endoscopic, gynecological, neurosurgical, ENT, dental, arthroscopic, orthopedic, plastic, reconstructive, prosthetic, muscle or tendon.

6. The method of claim 1 wherein said involved surfaces coated with said solution of polymeric material comprise tissue or surgical article surfaces or both.

7. A surgical article having surfaces adapted for contacting tissue surfaces during surgery, said surfaces of said surgical article having a wet coating thereon, said wet coating comprising a physiologically acceptable aqueous solution of a hydrophilic, polymeric material wherein:
   (a) the polymeric material is (1) a substantially water-soluble polymer having at least one $C_nF_{2n+1}$ substituent wherein $n \geq 4$, having a molecular weight of less than about 60,000; (2) a pharmaceutically acceptable salt or complex thereof; or (3) mixtures thereof; and
   (b) the concentration in said aqueous solution of said polymeric material is in the range of from about 0.1% to about 5.0% by weight; said molecular weight and concentration having values such that said aqueous solution is capable of providing wet coatings on said tissue.

8. The article of claim 7 wherein said polymeric material is polyethylene glycol terminated at both ends with $C_nF_{2n+1}$ groups wherein $n \geq 4$.

9. The article of claim 8 wherein said $C_nF_{2n+1}$ group is $C_8F_{17}$.

10. The article of claim 7 wherein said polymeric material is selected from the group consisting of polyacrylamides, polydimethylacrylamides, polyvinylpyrrolidones, neutral polysaccharides, ionic polysaccharides, polypeptides and mixtures thereof.

11. A method of protecting from damage tissues or organs during harvesting thereof from animals or humans, manufacture therefrom of bioprostheses and subsequent manipulations and implantations of said bioprostheses in animals or humans, comprising providing said tissue or organ surfaces with a wet coating of a physiologically acceptable aqueous solution of a hydrophilic, polymeric material prior to and during said harvesting, manufacture of bioprostheses, manipulations and implantations thereof, wherein:
   (a) the polymeric material is (1) a substantially water-soluble polymer having at least one $C_nF_{2n+1}$ substituent wherein $n \geq 4$, having a molecular weight of less than about 60,000; (2) a pharmaceutically acceptable salt or complex thereof; or (3) mixtures thereof; and
   (b) the concentration in said aqueous solution of said polymeric material is in the range of from about 0.1% to about 5.0% by weight; said molecular weight and concentration having values such that said aqueous solution is capable of providing wet coatings on said tissue.

12. The method of claim 11 wherein said polymeric material is polyethylene glycol terminated at both ends with $C_nF_{2n+1}$ groups wherein $n \geq 4$.

13. The method of claim 12 wherein said $C_nF_{2n+1}$ group is $C_8F_{17}$.

14. The method of claim 11 wherein said polymeric material is selected from the group consisting of polyacrylamides, polydimethylacrylamides, polyvinylpyrrolidones, neutral polysaccharides, ionic polysaccharides, polypeptides and mixtures thereof.

15. A bioprosthesis comprised at least in part of tissue or an organ or part thereof of an animal or human, said tissue or organ or part thereof having a coating thereon of a physiologically acceptable aqueous solution of a hydrophilic, polymeric material to protect said tissue or organ or part thereof from damage arising during harvesting thereof from said animal or human, manufacture of said bioprosthesis and manipulations and implantations of said bioprosthesis in animals or humans, wherein:
   (a) the polymeric material is (1) a substantially water-soluble polymer having at least one $C_nF_{2n+1}$ substituent wherein $n \geq 4$, having a molecular weight of less than about 60,000; (2) a pharmaceutically acceptable salt or complex thereof; or (3) mixtures thereof; and
   (b) the concentration in said aqueous solution of said polymeric material is in the range of from about 0.1% to about 5.0% by weight; said molecular weight and concentration having values such that said aqueous solution is capable of providing wet coatings on said tissue.

16. The bioprosthesis of claim 15 wherein said polymeric material is polyethylene glycol terminated at both ends with $C_nF_{2n+1}$ groups wherein $n \geq 4$.

17. The bioprosthesis of claim 16 wherein said $C_nF_{2n+1}$ group is $C_8F_{17}$.

18. The bioprosthesis of claim 15 wherein said polymeric material is selected from the group consisting of polyacrylamides, polydimethylacrylamiides, polyvinylpyrrolidones, neutral polysaccharides, ionic polysaccharides, polypeptides and mixtures thereof.

19. A method of protecting from damage tissues or organs or parts thereof during harvesting thereof from animals or humans, subsequent manipulations and implantations of said tissues or organs or parts thereof in animals or humans, comprising providing said tissue and organ surfaces with a wet coating of a physiologically acceptable aqueous solution of a hydrophilic, polymeric material prior to and during said harvesting, manipulations and implantations thereof, wherein:

(a) the polymeric material is (1) a substantially water-soluble polymer having at least one $C_nF_{2n+1}$ substituent wherein $n \geq 4$, having a molecular weight of less than about 60,000; (2) a pharmaceutically acceptable salt or complex thereof; or (3) mixtures thereof; and (b) the concentration in said aqueous solution of said polymeric material is in the range of from about 0.1% to about 5.0% by weight; said molecular weight and concentration having values such that said aqueous solution is capable of providing wet coatings on said tissue.

20. The method of claim 19 wherein said polymeric material is polyethylene glycol terminated at both ends with $C_nF_{2n+1}$ groups wherein $n \geq 4$.

21. The method of claim 20 wherein said $C_nF_{2n+1}$ group is $C_8F_{17}$.

22. The method of claim 19 wherein said polymeric material is selected from the group consisting of polyacrylamides, polydimethylacrylamides, polyvinylpyrrolidones, neutral polysaccharides, ionic polysaccharides, polypeptides and mixtures thereof.

* * * * *

UNITED STATES PATENT AND TRADEMARK OFFICE
CERTIFICATE OF CORRECTION

PATENT NO. : 6,090,997
DATED : July 18, 2000
INVENTOR(S) : Eugene P Goldberg et al. et al.

It is certified that error appears in the above-indentified patent and that said Letters Patent is hereby corrected as shown below:

In Claim 4, line 3, change "polydimethylacrylanides" to --polydimethylacrylamides--.

In Claim 18, line3, change "polydimethylacrylamiides" to --polydimethylacrylamides--.

Signed and Sealed this

Seventeenth Day of April, 2001

*Attest:*

NICHOLAS P. GODICI

*Attesting Officer*     *Acting Director of the United States Patent and Trademark Office*